(12) United States Patent
Quam et al.

(10) Patent No.: US 10,555,905 B2
(45) Date of Patent: Feb. 11, 2020

(54) QUICK RELEASE SOLENOID ASSEMBLY

(71) Applicant: Graco Minnesota Inc., Minneapolis, MN (US)

(72) Inventors: Paul R. Quam, Richland, WA (US); Matthew R. Theisen, Woodbury, MN (US); Parker J. Haffley, Hudson, WI (US)

(73) Assignee: Graco Minnesota Inc., Minneapolis, MN (US)

( * ) Notice: Subject to any disclaimer, the term of this patent is extended or adjusted under 35 U.S.C. 154(b) by 0 days.

(21) Appl. No.: 16/361,439

(22) Filed: Mar. 22, 2019

(65) Prior Publication Data

US 2019/0216732 A1    Jul. 18, 2019

Related U.S. Application Data

(63) Continuation of application No. 15/521,815, filed as application No. PCT/US2015/057383 on Oct. 26, 2015, now Pat. No. 10,278,921.
(Continued)

(51) Int. Cl.
*A61K 9/02* (2006.01)
*A61K 9/00* (2006.01)
(Continued)

(52) U.S. Cl.
CPC .............. *A61K 9/02* (2013.01); *A61K 9/0034* (2013.01); *A61K 31/194* (2013.01);
(Continued)

(58) Field of Classification Search
CPC ...... A61K 9/02; A61K 9/0034; A61K 31/194; A61K 31/201; A61K 33/00; A61K 47/02;
(Continued)

(56) References Cited

U.S. PATENT DOCUMENTS 3,111,139 A   11/1963   Beckett et al.
3,140,073 A    7/1964   Finck, Jr.
(Continued)

FOREIGN PATENT DOCUMENTS

| CN | 200988025 Y | 12/2007 |
| CN | 200988026 Y | 12/2007 |
| CN | 103998143 A | 8/2014 |

OTHER PUBLICATIONS

International Search Report and Written Opinion for PCT Application No. PCT/US2015/057383, dated Jan. 18, 2016, pp. 8.
(Continued)

*Primary Examiner* — Donnell A Long
(74) *Attorney, Agent, or Firm* — Kinney & Lange, P.A.

(57) ABSTRACT

A retaining system for a solenoid assembly of a liquid adhesive dispensing system includes a quick-release mechanism configured to secure the solenoid assembly in place. The quick-release mechanism engages an air tube of the solenoid and thereby secures the entire solenoid assembly to a manifold. The quick-release mechanism can release the solenoid, facilitating easy removal of the entire solenoid assembly, by a simple turning, pushing, or pulling action on the quick-release mechanism. The released solenoid can then be removed and replaced, thereby minimizing downtime caused due to the replacement of a faulty solenoid.

20 Claims, 8 Drawing Sheets

Related U.S. Application Data

(60) Provisional application No. 62/069,088, filed on Oct. 27, 2014.

(51) Int. Cl.
*A61K 31/194* (2006.01)
*A61K 31/201* (2006.01)
*A61K 33/00* (2006.01)
*A61K 47/02* (2006.01)
*B05B 7/16* (2006.01)
*B05B 7/24* (2006.01)
*B05B 13/02* (2006.01)

(52) U.S. Cl.
CPC ............ *A61K 31/201* (2013.01); *A61K 33/00* (2013.01); *A61K 47/02* (2013.01); *B05B 7/1606* (2013.01); *B05B 7/1666* (2013.01); *B05B 7/2491* (2013.01); *B05B 13/02* (2013.01)

(58) Field of Classification Search
CPC ... B05B 7/1606; B05B 7/1666; B05B 7/2491; B05B 13/02; B05C 5/0237; B05C 5/0279; B05C 11/1026
See application file for complete search history.

(56) References Cited

U.S. PATENT DOCUMENTS

| | | | |
|---|---|---|---|
| 3,598,360 A | 8/1971 | Merriner | |
| 4,889,316 A | 12/1989 | Donahue, Jr. | |
| 5,222,524 A | 6/1993 | Sekler et al. | |
| 5,407,101 A | 4/1995 | Hubbard | |
| 5,829,480 A | 11/1998 | Smith, III | |
| 5,887,768 A * | 3/1999 | Price | B05C 5/0225 222/486 |
| 6,060,125 A | 5/2000 | Fujii | |
| 6,425,416 B1 | 7/2002 | Narita et al. | |
| 6,598,279 B1 | 7/2003 | Morgan | |
| 6,733,044 B2 | 5/2004 | Huang | |
| 6,832,788 B2 | 12/2004 | Fukano et al. | |
| 7,316,244 B2 | 1/2008 | Miyazoe et al. | |
| 7,370,674 B2 | 5/2008 | Doyle | |
| 7,857,173 B2 | 12/2010 | Bolyard, Jr. | |
| 7,871,058 B2 | 1/2011 | Robinson et al. | |
| 2001/0042506 A1 | 11/2001 | Hogan et al. | |
| 2003/0205588 A1 | 11/2003 | Lee Mainous et al. | |
| 2006/0108553 A1 | 5/2006 | Mora | |
| 2008/0006658 A1 | 1/2008 | Bolyard | |
| 2008/0317559 A1 | 12/2008 | White et al. | |
| 2010/0218992 A1 | 9/2010 | Smith | |
| 2010/0269648 A1 | 10/2010 | Fenstemaker | |
| 2011/0300295 A1 | 12/2011 | Clark et al. | |
| 2012/0258246 A1 | 10/2012 | Saine et al. | |
| 2014/0299680 A1 | 10/2014 | Muller et al. | |
| 2015/0198271 A1 | 7/2015 | Wright | |
| 2015/0233524 A1 | 8/2015 | Kuo | |
| 2015/0235549 A1 | 8/2015 | Limbert et al. | |
| 2016/0061367 A1 | 3/2016 | Smith et al. | |

OTHER PUBLICATIONS

International Preliminary Report on Patentability for PCT Application No. PCT/US2015/057383, dated May 2, 2017, pp. 6.
First Chinese Office Action for CN Application No. 201580058224.0, dated Oct. 31, 2018, pp. 21.

* cited by examiner

QUICK RELEASE SOLENOID ASSEMBLY

CROSS-REFERENCE TO RELATED APPLICATIONS

This application is a continuation of U.S. application Ser. No. 15/521,815 filed Apr. 25, 2017 for "QUICK RELEASE SOLENOID ASSEMBLY" by P. R. Quam, M. R. Theisen and P. R. Haffley, and claims priority to International Application No. PCT/US2015/57383 filed Oct. 26, 2015 for "QUICK RELEASE SOLENOID ASSEMBLY" by P. R. Quam, M. R. Theisen and P. R. Haffley and to U.S. Provisional Application No. 62/069,088 filed Oct. 27, 2014, and entitled "QUICK REPLACE HOTMELT SOLENOID ASSEMBLY," the disclosures of which are hereby incorporated by reference in their entirety.

BACKGROUND

The present disclosure relates generally to systems for dispensing liquid adhesive. More particularly, the present disclosure relates to the retaining system for solenoid assemblies used to actuate dispensing modules.

Hot melt dispensing systems are typically used in manufacturing assembly lines to automatically disperse an adhesive used in the construction of packaging materials such as boxes, cartons and the like. Hot melt dispensing systems conventionally comprise a material tank, heating elements, a pump and a dispenser. Solid polymer pellets are melted in the tank using a heating element before being supplied to the dispenser by the pump. Because the melted pellets will re-solidify into solid form if permitted to cool, the melted pellets must be maintained at temperature from the tank to the dispenser. This typically requires placement of heating elements in the tank, the pump and the dispenser, as well as heating any tubing or hoses that connect those components. Furthermore, conventional hot melt dispensing systems typically utilize tanks having large volumes so that extended periods of dispensing can occur after the pellets contained therein are melted. However, the large volume of pellets within the tank requires a lengthy period of time to completely melt, which increases start-up times for the system. For example, a typical tank includes a plurality of heating elements lining the walls of a rectangular, gravity-fed tank such that melted pellets along the walls prevents the heating elements from efficiently melting pellets in the center of the container. The extended time required to melt the pellets in these tanks increases the likelihood of "charring" or darkening of the adhesive due to prolonged heat exposure.

Hot melt dispensing systems typically utilize a solenoid valve mounted to the system to actuate the dispensers between an open position and a closed position. Solenoid failures are one of the most common failures on hot melt dispensers. However, solenoid mountings require either multiple fasteners to hold the solenoid assembly in place, or require the user to perform multiple actions, such as pulling in one place and pushing in another, to attach and detach the solenoid assembly.

SUMMARY

According to one embodiment, a fluid dispensing system includes a manifold, a dispensing module, a solenoid assembly, and a quick-release mechanism. The manifold includes a fluid inlet, a fluid outlet, a fluid flow path extending through the manifold between the fluid inlet and the fluid outlet, and a plurality of air tube openings. The dispensing module is fluidly connected to the manifold, and the dispensing module is configured to receive a liquid adhesive through the fluid outlet and to dispense the liquid adhesive. The solenoid assembly is mounted to the manifold and configured to actuate the dispensing module between an open position and a closed position. The solenoid assembly includes a solenoid valve, the solenoid valve including an air inlet and an exhaust port, and a plurality of air tubes connected to the solenoid valve. The plurality of air tubes are configured to be received within the plurality of air tube openings of the manifold. The quick-release mechanism extends into the manifold and engages at least one of the plurality of air tubes, such that the quick-release mechanism secures the solenoid assembly to the manifold.

According to another embodiment, a liquid adhesive dispensing system includes a container for storing adhesive pellets, a melter capable of heating the adhesive pellets into a liquid adhesive, a feed system for transporting the adhesive pellets from the container to the melter, a supply system for transporting the liquid adhesive from the melter, and a dispensing system for receiving the liquid adhesive from the supply system and administering the liquid adhesive. The dispensing system includes a manifold, a dispensing module fluidly connected to the manifold, a solenoid assembly mounted to the manifold, and a quick release mechanism extending into the manifold. The manifold includes a fluid path and an air path. The fluid path includes a fluid inlet for receiving liquid adhesive from the supply system, a fluid outlet, and a fluid flow path extending between the fluid inlet and the fluid outlet. The air path includes a plurality of air tube openings extending into the manifold, a first module actuation opening, a second module actuation opening, a first air flow path extending between and connecting a first one of the air tube openings and the first module actuation opening, and a second air flow path extending between and connecting a second one of the air tube openings and the second module actuation opening. The dispensing module is configured to receive the liquid adhesive from the fluid outlet, to receive compressed air from the first module actuation opening, and to expel compressed air through the second module actuation opening. The solenoid assembly includes a solenoid valve and a plurality of air tubes. The solenoid valve includes an air inlet and an exhaust port. The plurality of air tubes are connected to the solenoid valve and are received within the plurality of air tube openings. The solenoid assembly is configured to actuate the dispensing module between an open position and a closed position by directing compressed air through the air tubes, through the first air flow path and the second air flow path, and to the dispensing module through the first module actuation opening and the second module actuation opening. The quick-release mechanism extends through the manifold and engages at least one of the plurality of air tubes, such that the quick-release mechanism secures the solenoid assembly to the manifold.

DETAILED DESCRIPTION

Figure 1:
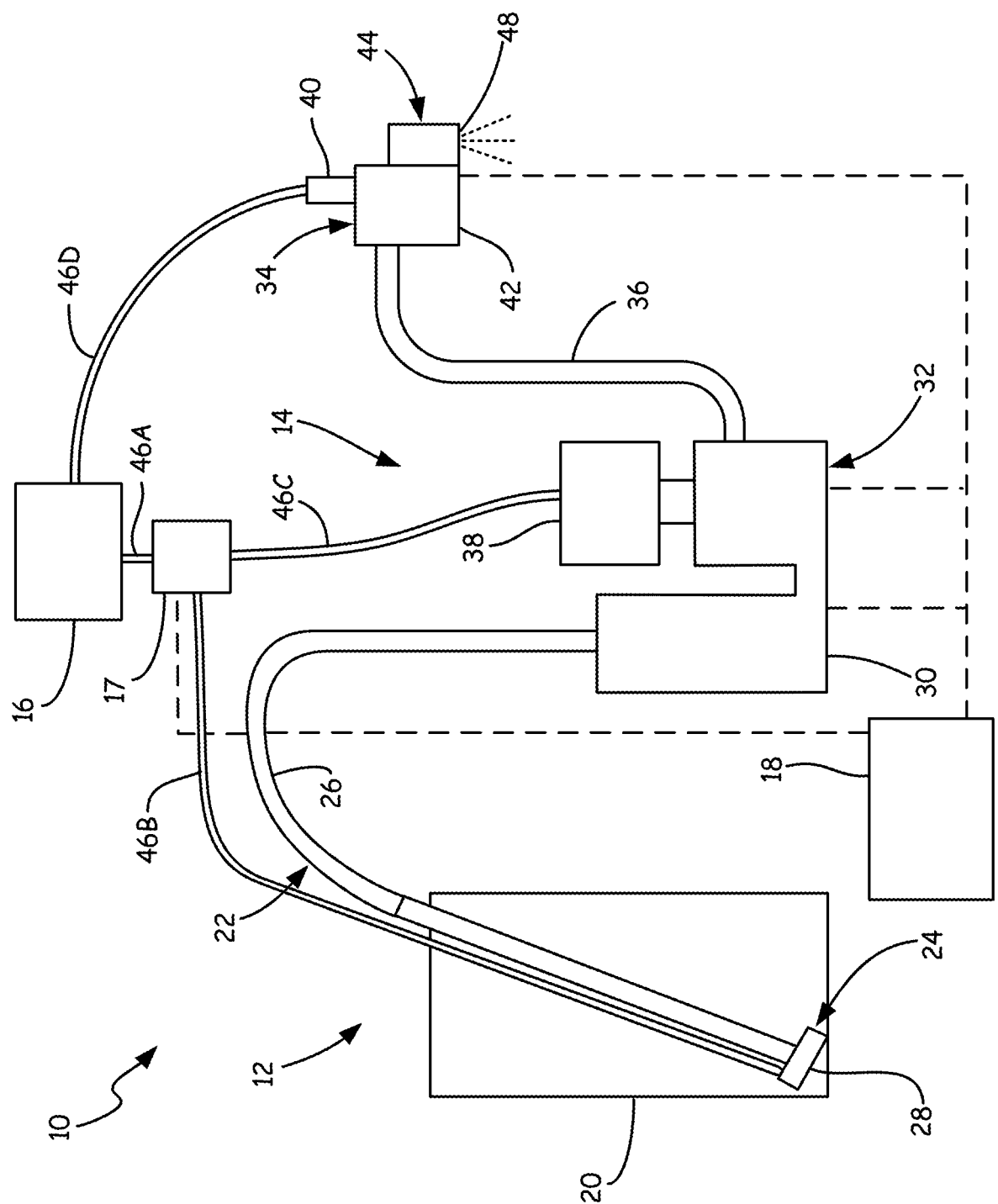
FIG. 1 is a schematic view of a system for dispensing liquid adhesive.

FIG. 1 is a schematic view of system 10 for dispensing liquid adhesive, such as hot melt adhesive for example. System 10 includes cold section 12, hot section 14, air source 16, air control valve 17, and controller 18. In the embodiment shown in FIG. 1, cold section 12 includes container 20 and feed assembly 22. Feed assembly 22 includes vacuum assembly 24, feed hose 26, and inlet 28. Hot section 14 includes melt system 30, pump 32, dispensing system 34, and supply hose 36. Pump 32 includes motor 38. Dispensing system 34 includes solenoid assembly 40, manifold 42, and dispensing module 44.

Air source 16 is a source of compressed air supplied to components of system 10 in both cold section 12 and hot section 14. Air control valve 17 is connected to air source 16 via air hose 46a, and air control valve 17 selectively controls air flow from air source 16 through air hose 46b to vacuum assembly 24 and through air hose 46c to motor 38 of pump 32. Air hose 46d connects air source 16 to solenoid assembly 40 of dispensing system 34, bypassing air control valve 17. Solenoid assembly 40 controls the flow of compressed air to dispensing module 44 to actuate dispensing module 44 between an open position, thereby dispensing liquid adhesive, and a closed position, thereby preventing liquid adhesive from being dispensed. Controller 18 is in communication with various components of system 10, such as air control valve 17, melt system 30, pump 32, and/or dispensing system 34 and various components thereof, for controlling the operation of system 10.

Components of cold section 12 can be operated at room temperature, without being heated. Container 20 can be a hopper for containing a quantity of solid adhesive pellets. Suitable adhesives can include, for example, a thermoplastic polymer glue such as ethylene vinyl acetate (EVA) or metallocene. Feed assembly 22 connects container 20 to hot section 14 for delivering the solid adhesive pellets from container 20 to hot section 14. Feed assembly 22 includes vacuum assembly 24 and feed hose 26. Vacuum assembly 24 is positioned in container 20. Compressed air from air source 16 is delivered to vacuum assembly 24 to create a vacuum, inducing a flow of solid adhesive pellets into inlet 28 of vacuum assembly 24 and then through feed hose 26 to hot section 14. Feed hose 26 is a tube or other passage sized with a diameter substantially larger than that of the solid adhesive pellets to allow the solid adhesive pellets to flow freely through feed hose 26. Feed hose 26 connects vacuum assembly 24 to hot section 14.

Solid adhesive pellets are delivered from feed hose 26 to melt system 30. Melt system 30 can include a tank and resistive heating elements for melting the solid adhesive pellets to form a liquid hot melt adhesive. Melt system 30 can be sized to have a relatively small adhesive volume, for example about 0.5 liters, and configured to melt solid adhesive pellets in a relatively short period of time. Pump 32 is driven by motor 38 to pump hot melt adhesive from melt system 30, through supply hose 36, and to dispensing system 34. Motor 38 can be an air motor driven by pulses of compressed air from air source 16 and air control valve 17. Pump 32 can be a linear displacement pump driven by motor 38.

Hot melt adhesive from pump 32 is received in manifold 42 and dispensed via dispensing module 44. Dispensing system 34 can selectively discharge hot melt adhesive through dispensing module 44, whereby the hot melt adhesive is sprayed out outlet 48 of dispensing module 44 onto an object, such as a package, a case, or another object benefiting from hot melt adhesive dispensed by system 10. Dispensing module 44 is actuated between an open mode, whereby the hot melt adhesive is sprayed out of outlet 48, and a closed mode, whereby the hot melt adhesive is prevented from spraying out of outlet 48, by solenoid assembly 40. Solenoid assembly 40 provides compressed air to dispensing module 44 to actuate dispensing module 44 between the open and the closed positions. Dispensing module 44 can be one of multiple modules that are part of dispensing system 34. Some or all of the components in hot section 14, including melt system 30, pump 32, supply hose 38, manifold 42, and dispensing module 44, can be heated to keep the hot melt adhesive in a liquid state during the dispensing process.

Figure 2A:
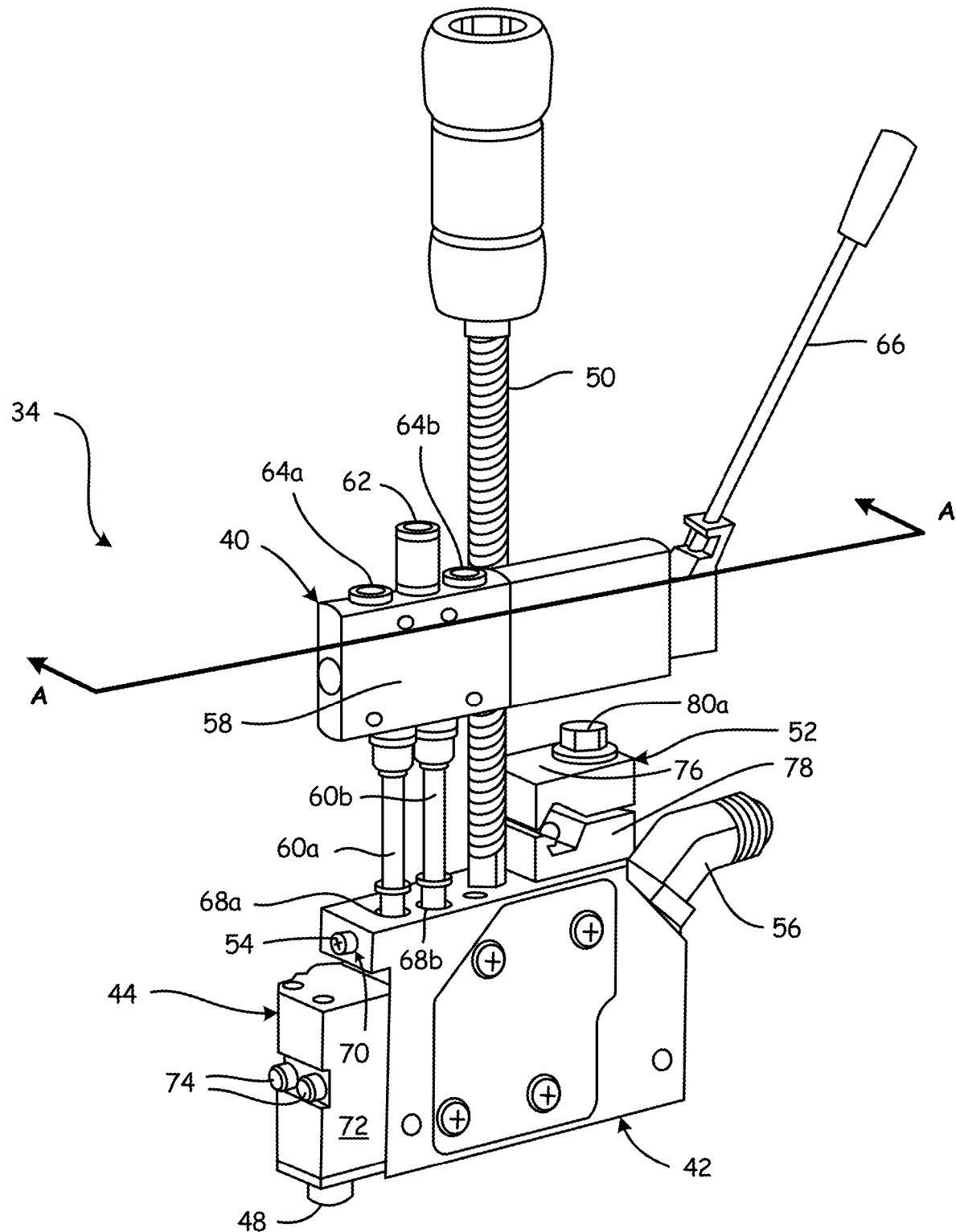
FIG. 2A is an isometric view of a dispensing system with a solenoid assembly attached.
Figure 2B:
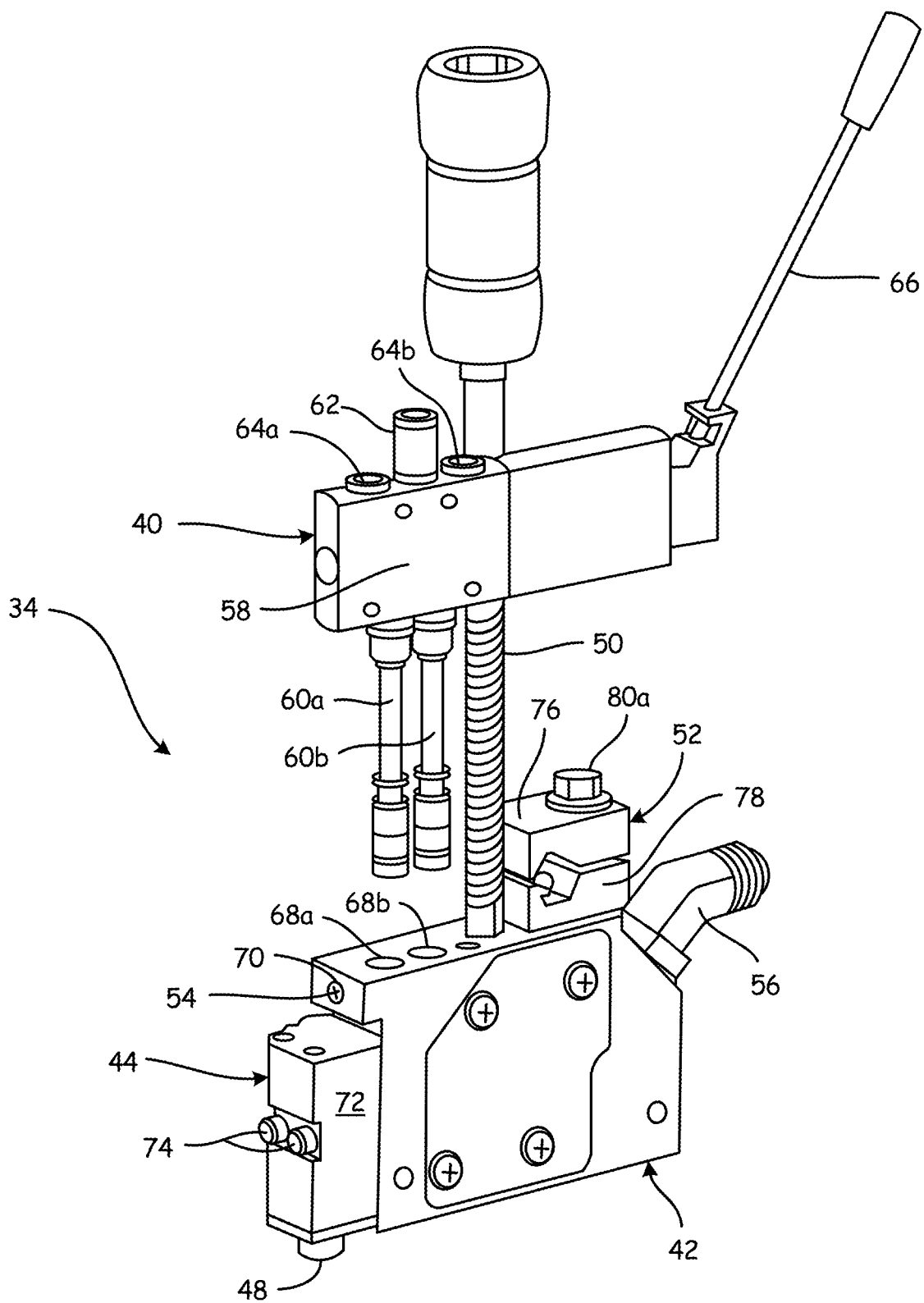
FIG. 2B is an isometric view of the dispensing system of FIG. 2A with the solenoid assembly detached.

FIG. 2A is a perspective view of dispensing system 34, including a single dispensing module 44, with solenoid assembly 40 attached. FIG. 2B is a perspective view of dispensing system 34 with solenoid assembly 40 detached. FIGS. 2A and 2B will be discussed together. Dispensing system 34 includes solenoid assembly 40, manifold 42, dispensing module 44, cordset 50, mounting clamp 52, quick release mechanism 54, and fluid inlet 56. Solenoid assembly 40 includes solenoid valve 58, air tubes 60a, 60b, air inlet 62, exhaust ports 64a, 64b, and solenoid cable 66. Manifold 42 includes air tube openings 68a, 68b and quick release opening 70. Dispensing module 44 includes outlet 48, body 72, and fasteners 74. Mounting clamp 52 includes upper portion 76, lower portion 78, and fasteners 80a and 80b (shown in FIG. 3).

Fluid inlet 56 is attached to manifold 42 and receives liquid adhesive from supply hose 36 (shown in FIG. 1). Dispensing module 44 is attached to manifold 42 by fasteners 74 passing through dispensing module 44 and into manifold 42. The liquid adhesive enters manifold through fluid inlet 56 and flows through manifold 42 to dispensing module 44, where the liquid adhesive is dispensed. Cordset 50 extends into manifold 42 and provides power to heating elements (not shown) within manifold 42. The heating elements ensure that the liquid adhesive flowing through manifold 42 remains in a liquid state.

Mounting clamp 52 is secured to a top of manifold 42. Fastener 80a passes through both upper portion 76 and lower portion 78 and into manifold 42. Fastener 80b passes through lower portion 78 and secures lower portion 78 to manifold 42. In this way, lower portion 78 may remain secured to manifold 42 while upper portion 76 may be removed to allow mounting clamp 52 to be positioned around a suitable mounting device, such as a mounting bar, to allow a user to position dispensing system 34 in any desired position.

Quick release mechanism 54 extends into quick release opening 70 of manifold 42. In the illustrated embodiment, quick release opening 70 is threaded such that quick release opening 70 receives a threaded quick release mechanism 54. It is understood, however, that quick release opening 70 and quick release mechanism 54 may be of any suitable combination to allow quick release mechanism 54 to be retained within but easily removable from quick release opening 70. For example, quick release opening 70 may be a smooth bore, while quick release mechanism 54 may be a detented dowel configured to engage a projection either within quick release opening 70 or on one of air tubes 60a, 60b.

Solenoid cable 66 is connected to and provides power to solenoid valve 58. Air tubes 60a, 60b are connected to solenoid valve 58. Air tube 60a is in fluid communication with air inlet 62 and exhaust port 64a. Similarly, air tube 60b is in fluid communication with air inlet 62 and exhaust port 64b. Solenoid valve 58 may be any suitable solenoid valve for directing compressed air through air tubes 60a, 60b and to dispensing module 44. For example, solenoid valve 58 may be a five-way exhausting solenoid valve with an internal piston that directs compressed air from air inlet 62 through one of air tubes 60a, 60b, while simultaneously allowing previously utilized compressed air to exhaust through the other one of air tube 60a, 60b and to the atmosphere through either exhaust port 64a or exhaust port 64b.

In FIG. 2A solenoid assembly 40 is shown attached to manifold 42. Air tubes 60a, 60b extend into air tube openings 68a, 68b, respectively. Air tubes 60a, 60b are freely slidable within air tube openings 68a, 68b unless secured by quick release mechanism 54. Quick release mechanism 54 extends into quick release opening 70 of manifold 42 and engages air tube 60a. As air tubes 60a and 60b are preferably rigid and as such quick release mechanism 54 engaging air tube 60a secures solenoid assembly 40 to manifold 42. While quick release mechanism 54 is described as engaging air tube 60a, it is understood that quick release mechanism may engage air tube 60b or both air tubes 60a and 60b.

In FIG. 2B solenoid assembly 40 is shown as detached from manifold 42. In the illustrated embodiment, quick release mechanism 54 is shown as a single set screw; it is understood however, that quick release mechanism 54 may take any suitable shape for securing solenoid assembly 40 to manifold 42 while still allowing a user to quickly and efficiently release and remove solenoid assembly 40. For example, quick release mechanism 54 may be a push piston, a detented dowel, a sheet metal cover, a hinged bracket, or any other suitable mechanism. In the illustrated embodiment, rotating quick release mechanism 54 within quick release opening 70 causes quick release mechanism 54 to disengage from air tube 58a, thereby freeing solenoid assembly 40. The user may then easily remove solenoid assembly 40 by simply pulling solenoid assembly 40 free from manifold 42. As shown, quick release mechanism 54 may remain partially within quick release opening 70, yet solenoid assembly may still be removed from manifold 42.

Quick release mechanism 54 allows a user to quickly remove and replace solenoid assembly 40, which minimizes any down time caused on an assembly line due to solenoid failures. Quick release mechanism 54 may be activated by a simple movement such as a turn, though it is understood that other embodiments of quick release mechanism may be activated through other simple movements, such as a push or pull.

Figure 3:
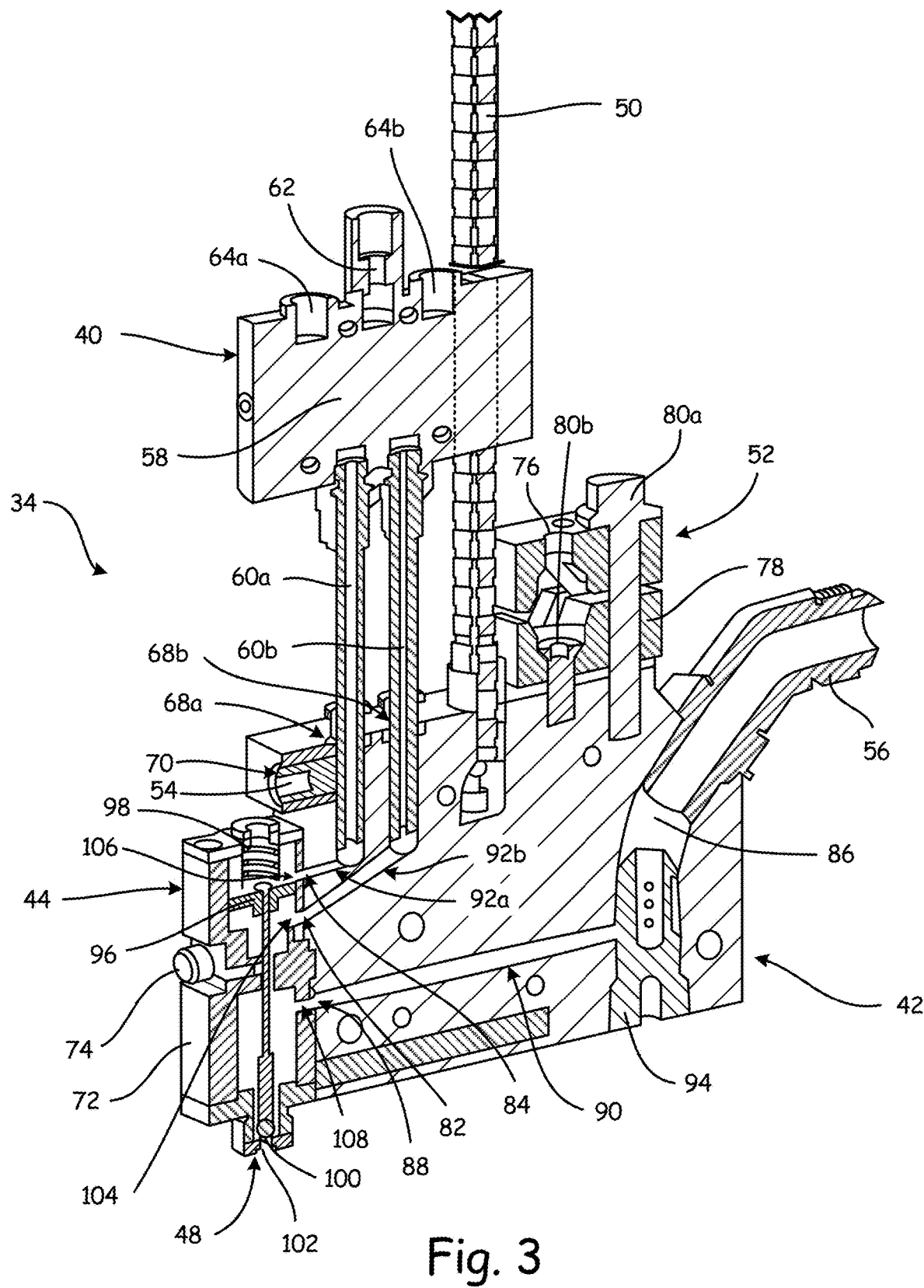
FIG. 3 is a cross-sectional view of the dispensing system of FIG. 2A taken along line A-A of FIG. 2A.
Figure 3A:
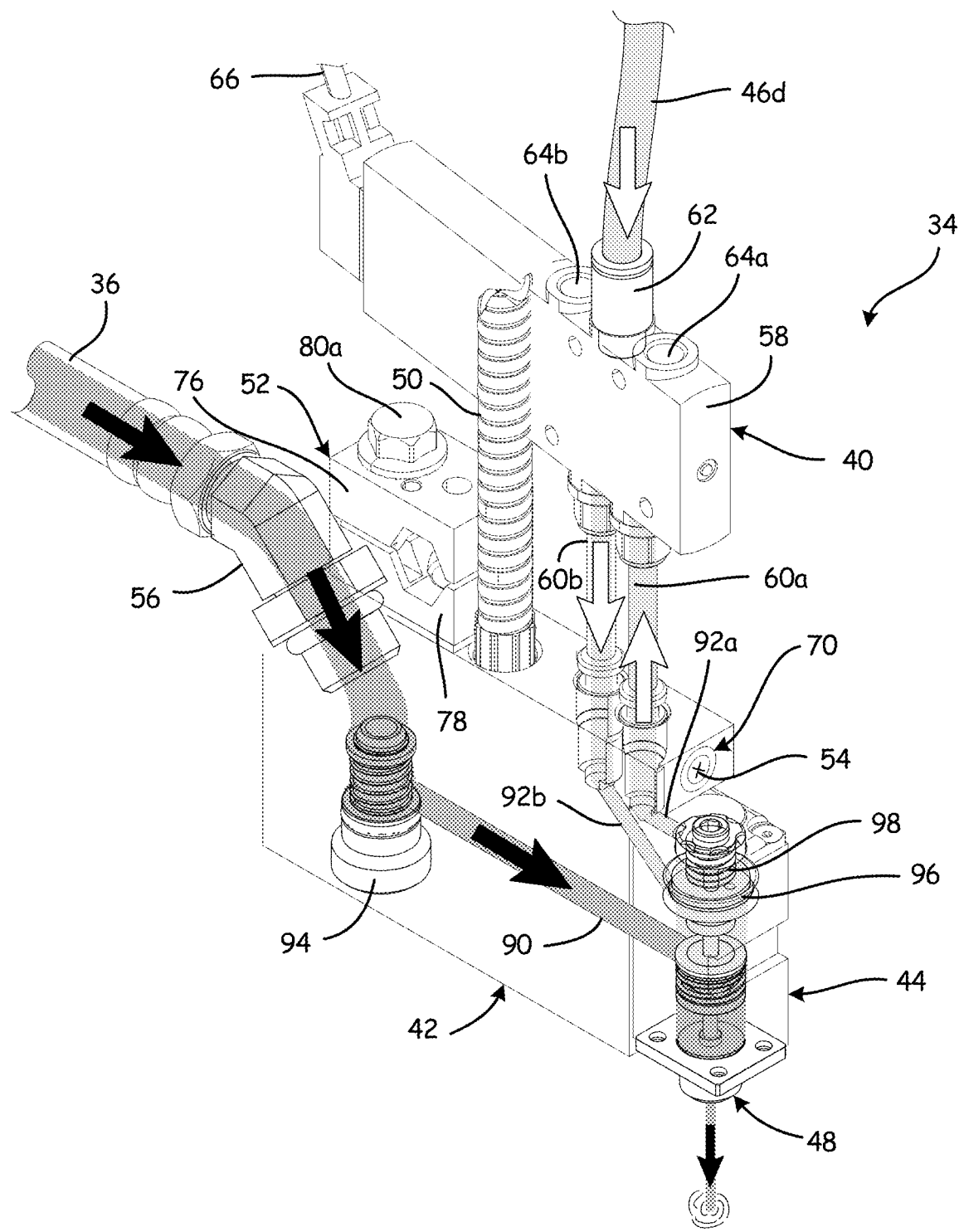
FIG. 3A is an isometric view of a dispensing system showing the flow of liquid adhesive and compressed air through the dispensing system.

FIG. 3 is a cross-sectional view of dispensing system 34 taken along line A-A in FIG. 2A. FIG. 3A is a perspective view of dispensing system 34 showing flow lines of liquid adhesive and compressed air through dispensing system 34. FIGS. 3 and 3A will be discussed together. Dispensing system 34 includes solenoid assembly 40, manifold 42, dispensing module 44, cordset 50, mounting clamp 52, quick release mechanism 54, and fluid inlet 56. Solenoid assembly 40 includes solenoid valve 58 (the internal components of which are not shown), air tubes 60a, 60b, air inlet 62, exhaust ports 64a, 64b, and solenoid cable 66 (shown in FIG. 3A). Manifold 42 includes air tube openings 68a, 68b, quick release opening 70, first module actuation opening 82, second module actuation opening 84, adhesive inlet 86, adhesive outlet 88, adhesive flow path 90, air flow paths 92a, 92b, and filter 94. Dispensing module 44 includes outlet 48, body 72, fasteners 74, piston 96, spring 98, ball 100, seat 102, open inlet 104, close inlet 106, and adhesive inlet 108. Mounting clamp 52 includes upper portion 76, lower portion 78, and fasteners 80a, 80b.

Fluid inlet 56 is connected to manifold 42 and secured within adhesive inlet 86. Adhesive flow path 90 extends between adhesive inlet 86 and adhesive outlet 88, and filter 74 is disposed within adhesive flow path 90. Fasteners 74 extend through dispensing module 44 and attach dispensing module 44 to manifold 42. When dispensing module 44 is attached to manifold 42, adhesive inlet 108 is aligned with adhesive outlet 88 to allow dispensing module 44 to receive liquid adhesive from manifold 42. Similarly, open inlet 104 is aligned with first module actuation opening 82 and close inlet 106 is aligned with second module actuation opening 84 such that dispensing module 44 may receive compressed air through manifold 42 to allow dispensing module 44 to be actuated between an open position and a closed position.

Piston 96 is disposed within body 72 of dispensing module and piston is arranged between open inlet 104 and close inlet 106. Spring 98 is disposed within body 72 on top of piston 96, and spring 98 biases piston 96 downward such that dispensing module 44 is in a normally-closed position when no compressed air is provided to dispensing module 44. Ball 100 is attached to an end of piston 96, and ball 100 rests in seat 106 to prevent liquid adhesive from exiting dispensing module 44.

Cordset 50 extends into manifold 42 and provides power to heating elements (not shown) within manifold 42. The heating elements ensure that the liquid adhesive flowing through manifold 42 remains in a liquid state. Mounting clamp 52 is secured to a top of manifold 42. Fastener 80a passes through both upper portion 76 and lower portion 78 and into manifold 42. Fastener 80b passes through lower portion 78 and secures lower portion 78 to manifold 42. In this way, lower portion 78 may remain secured to manifold 42 while upper portion 76 may be removed to allow mounting clamp 52 to be positioned around a suitable mounting device, such as a mounting bar, to allow a user to position dispensing system 34.

Quick release mechanism 54 extends into quick release opening 70 of manifold 52. Quick release mechanism 54 is configured to engage at least one of air tubes 60a, 60b thereby securing solenoid assembly 40 to manifold 42. In the illustrated embodiment, quick release mechanism 54 is a set screw configured to engage air tube 60a. Engaging air tube 60a secures solenoid assembly 40 to manifold 42 as air tube 60a is preferably constructed of a rigid material, such as aluminum, and air tube 60a is connected to solenoid valve 56. It is understood that quick release mechanism 54 may take any suitable form for engaging at least one of air tubes 60a, 60b. For example, air tubes 60a, 60b may include an exterior threading and quick release mechanism 54 may be configured with compatible threading such that quick release mechanism 54 passes by and engages the external threading of both air tube 60a and air tube 60b. Quick release mechanism 54 allows a user to quickly detach, with a simple twist, push, or pull, solenoid assembly 40 from manifold 42 and replace solenoid assembly 40 in case of a failure of solenoid assembly 40.

Air tubes 60a, 60b are connected to solenoid valve 58 and extend into air tube openings 68a, 68b of manifold 42, respectively. Air flow path 92a extends through manifold 42 between air tube 60a and second module actuation opening 84. In this way, compressed air may be provided to dispensing module 44 through air inlet 62, solenoid valve 58, air tube 60a, air flow path 92a, second module actuation opening 84, and close inlet 106. Compressed air may also be exhausted from dispensing module 44 through close inlet 106, second module actuation opening 84, air flow path 92a, air tube 60a, solenoid valve 58, and exhaust port 64a. Similarly, air flow path 92b extends through manifold 42 between air tube 60b and first module actuation opening 82. In this way, compressed air may be provided to dispensing module 44 through air inlet 62, solenoid valve 58, air tube 60b, air flow path 92b, first module actuation opening 82, and open inlet 104. Compressed air may also be exhausted from dispensing module 44 through open inlet 104, first module actuation opening 82, air flow path 92b, air tube 60b, solenoid valve 58, and exhaust port 64b.

As shown in FIG. 3A, dispensing module 44 is typically in a closed position, as previously discussed. To actuate dispensing module 44 from a closed position to an open position, a first portion of compressed air is provided through air hose 46d and enters solenoid valve 58 through air inlet 62. Solenoid valve 58 directs the first portion of compressed air through air tube 60b and the first portion of compressed air enters manifold 42. The first portion of compressed air flows through air flow path 92b and exits manifold 42 through first module actuation opening 82. The first portion of compressed air then enters dispensing module 44 through open inlet 104 (best seen in FIG. 3), and the first portion of compressed air forces piston 96 up, overcoming the force of spring 98. With piston 96 forced up, ball 100 (shown in FIG. 3) disengages from seat 102 (shown in FIG. 3), thereby allowing liquid adhesive to exit dispensing module 44 through outlet 48.

The liquid adhesive is provided to dispensing system 34 through supply hose 36 (shown in FIG. 1). The liquid adhesive enters fluid inlet 56 from supply hose 36 and enters manifold 42 through adhesive inlet 86. The liquid adhesive flows along adhesive flow path 90 and exits manifold 42 through adhesive outlet 88. While the liquid adhesive is flowing through manifold 42, cordset 50 provides power to heating elements (not shown) located within manifold 42, and the heating elements provide sufficient heat to the liquid adhesive to prevent the liquid adhesive from solidifying within manifold 42. After the liquid adhesive exits adhesive outlet 88, the liquid adhesive enters dispensing module 44 through adhesive inlet 108. The liquid adhesive is then dispensed onto a desired surface through outlet 48.

After the liquid adhesive is applied to the desired surface, the flow of liquid adhesive through dispensing module 44 may be shut off. Solenoid valve 56 is actuated such that a second portion of compressed air is directed to air tube 60a instead of air tube 60b. Shifting solenoid valve 56 also opens a flow path through solenoid valve 56 between air tube 60b and exhaust port 64b. The second portion of compressed air exits solenoid valve 56 through air tube 60a and flows through air flow path 92a to dispensing module 44. The second portion of compressed air enters dispensing module 44 through close inlet 106 (best seen in FIG. 3), and the second portion of compressed air, aided by spring 98, forces piston 96 down. As piston 96 is forced down, ball 100 reengages seat 102, thereby shutting off the flow of liquid adhesive through outlet 48.

While piston 96 is shifting from the up position to the down position, the first portion of compressed air is forced out of dispensing module 44. The first portion of compressed air exits dispensing module 44 through open inlet 104 (best seen in FIG. 3) and enters air flow path 92b. The first portion of compressed air flows back through air flow path 92b and through air tube 60b. The first portion of compressed air is then exhausted to the atmosphere through exhaust port 64b. It is understood that the second portion of compressed air is similarly exhausted through exhaust port 64a when piston 96 is actuated from the closed to the open position.

Figure 4:
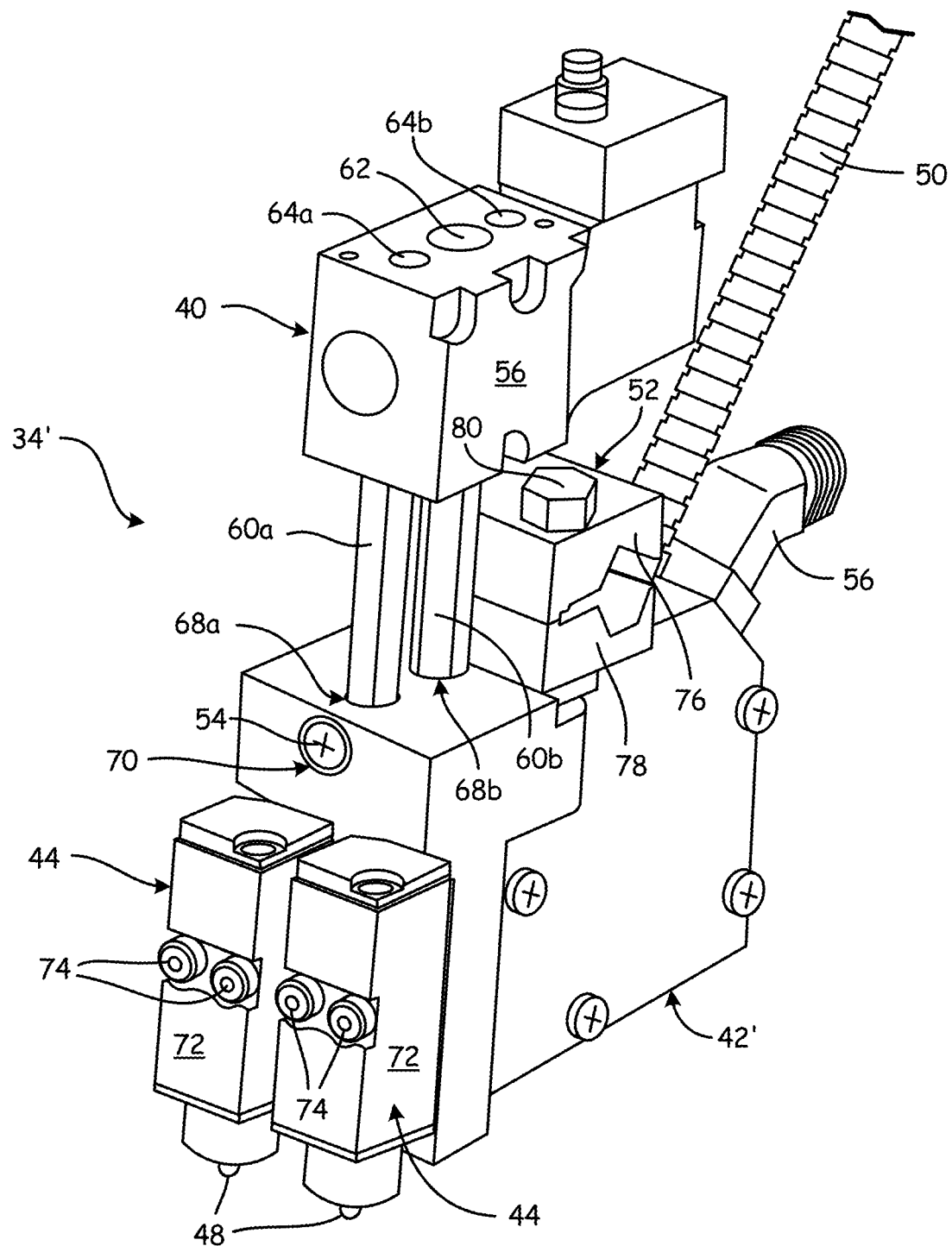
FIG. 4 is an isometric view of an embodiment of a dispensing system with multiple dispensing modules.

FIG. 4 is a perspective view of dispensing system 34' with multiple dispensing modules 44. Dispensing system 34' is similar to dispersing system 34, and similar reference numbers are used to identify similar components. Dispensing system 34' includes solenoid assembly 40, manifold 42', dispensing modules 44, cordset 50, mounting clamp 52, quick release mechanism 54, and fluid inlet 56. Solenoid assembly 40 includes solenoid valve 56, air tubes 60a, 60b, air inlet 62, exhaust ports 64a, 64b, and solenoid cable 66 (best seen in FIG. 2A). In the present embodiment, air tubes 60a, 60b are rigid tubes connected to solenoid valve 56 and received by manifold 42'. Manifold 42' includes air tube openings 68a, 68b and quick release opening 70. Dispensing modules 44 each include outlet 48, body 72, and fasteners 74.

Fluid inlet 56 is mounted to manifold 42', and fluid inlet 56 connects to supply hose 36 (shown in FIG. 1) to allow liquid adhesive to enter manifold 42'. Cordset 50 is attached to manifold 42' and provides power to heating elements (not shown) contained within manifold 42'. Mounting clamp 52 includes upper portion 76, lower portion 78, and fasteners 80. Upper portion 76 and lower portion 78 are secured together by fasteners 80, and fasteners 80 also secure mounting clamp 52 to manifold 42'. Quick release mechanism 54 extends into manifold 42' and is configured to engage at least one of air tubes 60a, 60b.

Mounting clamp 52 is configured to secure dispensing system 34' at a desired position for dispensing liquid adhesive. Upper portion 76 and lower portion 78 are fitted around a suitable positioning mechanism, such as a mounting bar, and upper portion 76 and lower portion 78 are secured together by fasteners 80 to lock dispensing system 34' in a desired position. Air tubes 60a, 60b provide a flow path for compressed air to flow from solenoid valve 56 to dispensing modules 44 to actuate dispensing modules 44 between an open position and a closed position.

Quick release mechanism 54 extends into manifold 42' through quick release opening 70, and quick release mechanism 54 engages at least one of air tubes 60a, 60b and thereby secures solenoid assembly 40 to manifold 42'. Quick release mechanism 54 engages an end of air tubes 60a and/or 60b extending into manifold 42'. Quick release mechanism 54 is configured to engage or disengage the air tubes 60a, 60b with a simple movement, such as a twist, push, or pull. In this way, quick release mechanism 54 allows a user to quickly detach and replace solenoid assembly 40 in case of a failure of solenoid assembly 40. Quickly detaching and replacing solenoid assembly 40 minimizes any downtime experienced on the assembly line due to solenoid failure.

Figure 5:
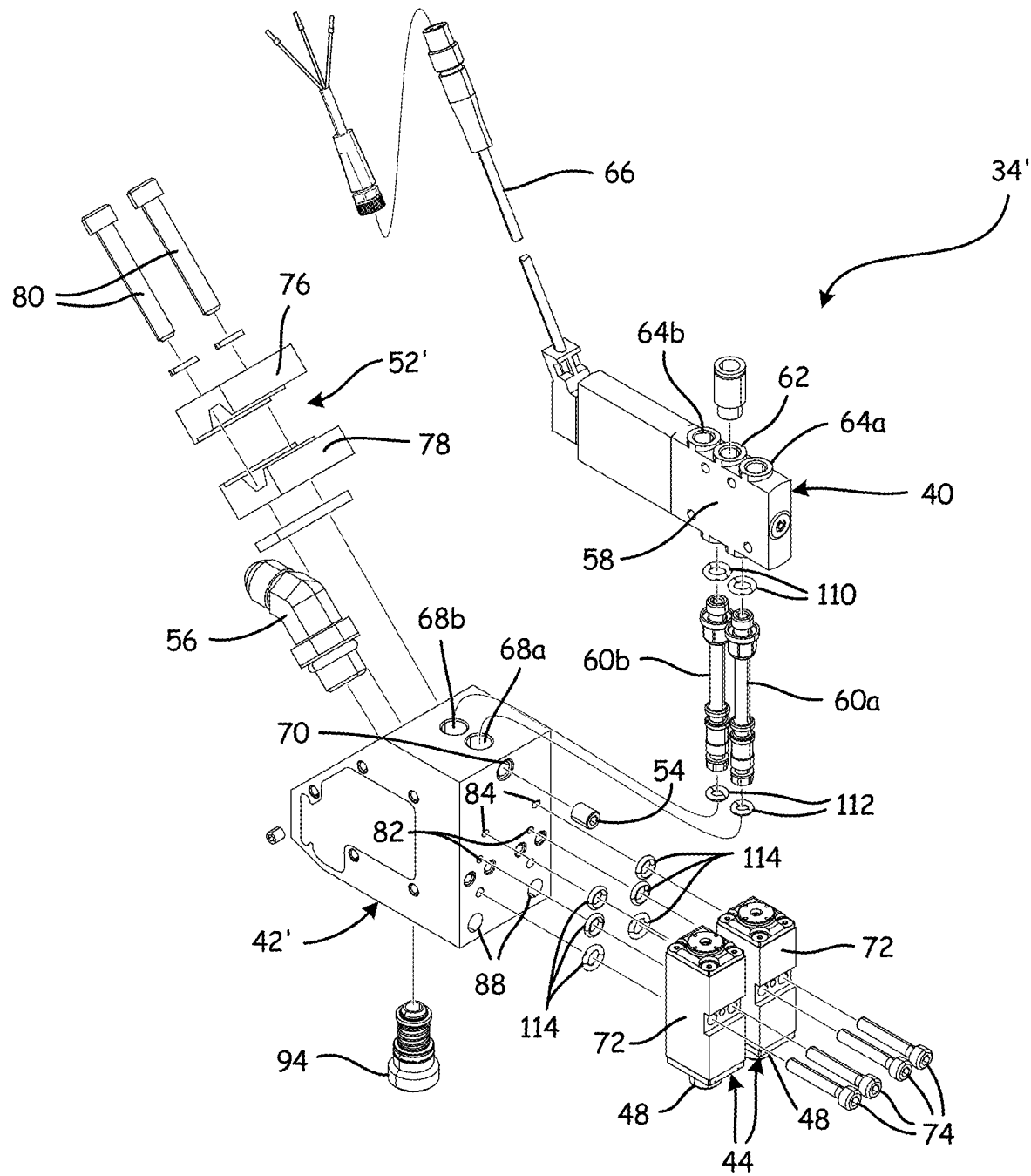
FIG. 5 is an exploded isometric view of a dispensing system with multiple dispensing modules.

FIG. 5 is an exploded, perspective view of dispensing system 34'. Dispensing system 34' includes solenoid assembly 40, manifold 42', dispensing modules 44, cordset 50 (shown in FIG. 4), mounting clamp 52', quick release mechanism 54, and fluid inlet 56. Solenoid assembly 40 includes solenoid valve 58, air tubes 60a, 60b, air inlet 62, exhaust ports 64a, 64b, and solenoid cable 66. Solenoid assembly 40 further includes o-rings 110 disposed between air tubes 60a, 60b and solenoid valve 58, and o-rings 112 disposed between air tubes 60a, 60b and manifold 42'. Manifold 42' is similar to manifold 42 (shown in FIG. 2A) with manifold 42' configured to provide compressed air and liquid adhesive to multiple dispensing modules 44. Manifold 42' includes filter 94, air tube openings 68a, 68b, first module actuation opening 82, second module actuation opening 84, quick release opening 70, and adhesive outlets 88. Dispensing modules 44 each include outlet 48, body 72, fasteners 74, and o-rings 114. Mounting clamp 52 includes upper portion 76, lower portion 78, and fasteners 80.

Solenoid cable 66 is connected to solenoid valve 58 and provides power to solenoid valve 58. O-rings 110 are disposed between air tubes 60a, 60b and solenoid valve 58 to ensure an air-tight connection of air tubes 60a, 60b to solenoid valve 58. O-rings 112 are disposed around air tubes 60a, 60b and positioned within air tube openings 68a, 68b of manifold 42' when solenoid assembly 40 is installed. O-rings 112 ensure an airtight connection of air tubes 60a, 60b to manifold 42'. Air tubes 60a, 60b are connected to both solenoid valve 58 and manifold 42' and provide flow paths for compressed air to enter and exit manifold 42'. Compressed air is provided through solenoid valve 58 from air source 16 (shown in FIG. 1) and to dispensing modules 44 to actuate dispensing modules 44 between open and closed positions.

Dispensing modules 44 are secured to manifold 42' by fasteners 74 extending through dispensing modules 44 and into manifold 42'. O-rings 114 are disposed between dispensing modules 44 and manifold 42'. More specifically, o-rings 114 are disposed about first module actuation openings 82, second module actuation openings 84, and adhesive outlets 88 to provide a sealed connection at the interface of dispensing modules 44 and manifold 42'. While dispensing system 34' is illustrated as including two dispensing modules 44, it is understood that dispensing system 34' may include as many or as few dispensing modules 44 as desired. It is also understood that manifold 42' may be configured to accept as many or as few dispensing modules 44 as desired. For example, where four dispensing modules 44 were desired, manifold would include four first module actuation openings 82, four second module actuation openings 84, and four adhesive outlets 88.

Mounting clamp 52' is secured to manifold 42'. Fasteners 80 extend through upper portion 76 and lower portion 78 and into manifold 42' to secure upper portion 76 and lower portion 78 together. Upper portion 76 and lower portion 78 may be arranged about any suitable positioning device, such as a mounting bar, to secure dispensing system 34' in a desired position.

Fluid inlet 56 is attached to manifold 42' and provides a fluid path for liquid adhesive to enter manifold 42' from supply hose 38 (best seen in FIG. 1). Liquid adhesive flows through supply hose 38 and to fluid inlet 56 and the liquid adhesive enters manifold 42' through fluid inlet 56. After entering manifold 42', the liquid adhesive is filtered by filter 74 and flows to dispensing modules 44 along adhesive flow path 90 (shown in FIG. 3). The liquid adhesive exits manifold 42' through adhesive outlets 88.

Quick release mechanism 54 extends through quick release opening 70 and is configured to engage at least one of air tubes 60a, 60b. Quick release mechanism 54 secures solenoid assembly 40 to manifold 42'. To disconnect solenoid assembly 40, quick release mechanism 54 may be loosened to allow air tubes 60a, 60b to be pulled out of air tube openings 68a, 68b. In this way, quick release mechanism 54 allows a user to quickly and efficiently remove solenoid assembly 40, which minimizes the downtime of system 10 due to any fault in solenoid assembly 40.

Quick release mechanism 54 secures solenoid assembly 40 to manifold 42'. Solenoid assembly 42' controls a flow of compressed air to dispensing modules 44 to actuate dispensing modules 44 between an open position, whereby liquid adhesive is dispensed through dispensing modules 44, and a closed position, whereby liquid adhesive is prevented from flowing through dispensing modules 44. To actuate dispensing module 44, compressed air is provided to solenoid valve 58 through air inlet 62. In one embodiment, solenoid valve 58 directs the compressed air through air tube 60b to actuate dispensing modules 44 from a closed position to an open position.

The compressed air is directed through air tube 60b and enters manifold 42' through air tube opening 68b. The compressed air then flows along air flow path 92b (shown in FIG. 3A) and exits manifold 42' through first module actuation opening 82. The compressed air enters dispensing modules 44 and actuates an internal piston 96 (shown in FIG. 3) thereby allowing liquid adhesive to exit dispensing modules 44 through outlets 48. The liquid adhesive enters manifold 42' through fluid inlet 56, flows along an internal adhesive flow path 90 and exits manifold 42' through adhesive outlet 88. After exiting adhesive outlet 88, the liquid adhesive flows through dispensing modules 44 and is dispensed through outlet 48.

Once a desired amount of liquid adhesive is applied, solenoid valve 58 shifts and compressed air is directed to dispensing manifolds 44 to actuate internal piston 96 back to the closed position. The compressed air entering solenoid valve 56 through air inlet 62 is directed through air tube 60a. At the same time, air tube 60b is now fluidly connected to exhaust port 64b allowing used compressed air to be exhausted from dispensing modules 44 through manifold 42', air tube 60b, and exhaust port 64b. The compressed air directed to air tube 60a enters manifold 42' through air tube opening 68a. The compressed air flows through manifold 42' along air flow path 92a (shown in FIG. 3) and exits manifold 42' through second module actuation opening 84. The compressed air enters dispensing modules 44 and actuates internal piston 96 to a closed position, thereby ceasing the flow of liquid adhesive through outlet 48.

Figure 6:
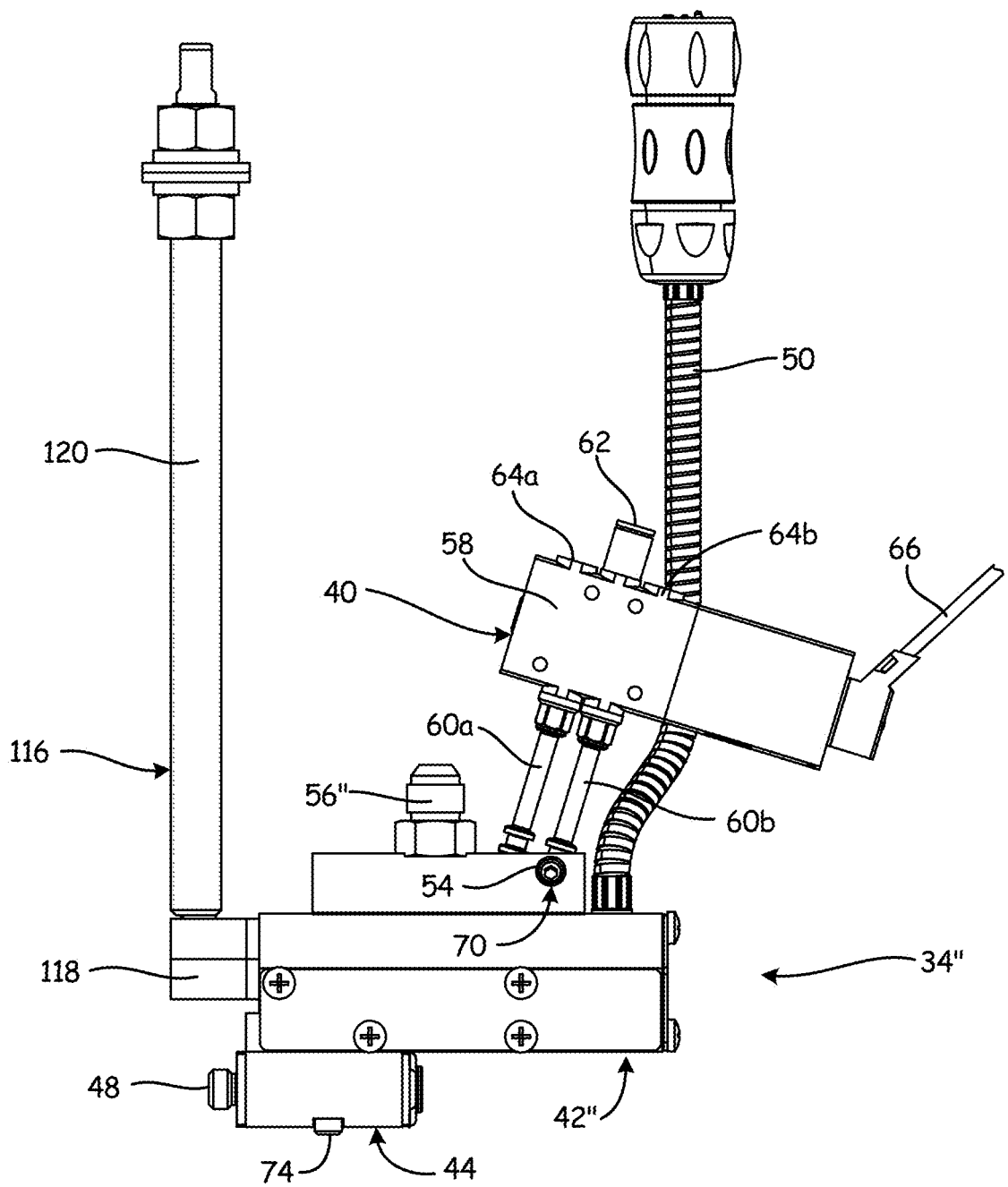
FIG. 6 is a side elevation view of yet another embodiment of the dispensing system with the dispensing module mounted on a bottom of the manifold.

FIG. 6 is a side elevation view of another embodiment of dispensing system 34". Dispensing system 34" is similar to dispensing system 34 and to dispensing system 34', and similar reference numbers are used to identify similar components. Dispensing system 34" includes solenoid assembly 40, manifold 42", dispensing modules 44, cordset 50, quick release mechanism 54, fluid inlet 56", and mount 116. Solenoid assembly 40 includes solenoid valve 58, air tubes 60a, 60b, air inlet 62, exhaust ports 64a, 64b, and solenoid cable 66. Manifold 42" includes quick release opening 70. Dispensing module 44 includes outlet 48 and fasteners 74. Mount 116 includes mounting block 118 and mounting rod 120.

Fluid inlet 56" is attached to a top portion of manifold 42" and is configured to receive liquid adhesive from supply hose 36 (shown in FIG. 1). Dispensing modules 44 are attached to a bottom of manifold 42". Liquid adhesive enters fluid inlet 56" and passes through an adhesive flow path disposed within manifold 42" and to dispensing modules 44. Cordset 50 extends into manifold 42" and cordset 50 provides power to heating elements (not shown) disposed within manifold 42". The heating elements ensure that the liquid adhesive remains in a liquid state as the liquid adhesive passes through manifold 42".

Mount 116 is secured to an end of manifold 42". Mounting block 118 is fastened to manifold 42" and may include a threaded opening (not shown). Mounting rod 120 may include a threaded end configured to engage the threaded opening of mounting block 118. It is understood that mounting block 118 may include a smooth opening with mounting rod 120 inserted into the opening, and mounting rod 120 may be configured to receive a fastener extending through mounting block 118 to secure mounting rod 120 relative to mounting block 118.

Solenoid cable 66 is connected to and provides power to solenoid valve 58. Air tubes 60a, 60b are connected to solenoid valve 58 and extend into manifold 42". Compressed air enters solenoid valve 58 and passes through either air tube 60a or air tube 60b to actuate dispensing modules 44. Used compressed air passes from dispensing modules 44 back through one of air tube 60a or air tube 60b and is exhausted to the atmosphere through exhaust port 64a or exhaust port 64b, respectively.

Quick release mechanism 54 extends into quick release opening 70 of manifold 42" and quick release mechanism 54 secures solenoid assembly 40 to manifold 42". Quick release mechanism 54 is configured to engage at least one of air tubes 60a, 60b. Alternatively, quick release mechanism 54 may extend between both air tube 60a and air tube 60b and thereby engage both air tubes 60a, 60b. By engaging at least one of air tubes 60a, 60b quick release mechanism 54 secures solenoid assembly 40 to manifold 42". In the illustrated embodiment, quick release mechanism 54 is a set screw configured to engage air tube 60b. To release solenoid assembly 40, quick release mechanism 54 may be activated by a simple turn such that quick release mechanism 54 no longer engages air tube 60b. In this way, solenoid assembly 40 may be easily and efficiently removed by simply turning quick release mechanism 54, which minimizes any downtime of system 10 (shown in FIG. 1) due to a faulty and/or failed solenoid.

Although the present invention has been described with reference to preferred embodiments, workers skilled in the art will recognize that changes may be made in form and detail without departing from the spirit and scope of the invention.

The invention claimed is:

1. A fluid dispensing system comprising:
   a manifold including a fluid outlet, a first tube opening extending into a first side of the manifold, and a second tube opening extending into the first side of the manifold; and a mount opening extending into a second side of the manifold and intersecting with the first tube opening;
   a dispensing module fluidly connected to the manifold and configured to receive a liquid adhesive from a fluid outlet of the manifold and to dispense the liquid adhesive;
   a solenoid assembly mounted to the manifold by a first air tube and a second air tube, wherein the solenoid assembly is configured to selectively direct air to the dispensing module to actuate the dispensing module between an open position and a closed position;
   wherein the first air tube extends into the first tube opening and the second air tube extends into the second tube opening;
   wherein a quick release mechanism is mounted in the mount opening, engages the first air tube, and does not engage the second air tube, such that the quick release mechanism is configured to directly secure the first air tube to the manifold and to indirectly secure the solenoid assembly and second air tube to the manifold by the first air tube.

2. The fluid dispensing system of claim 1, wherein the plurality of air tubes comprise rigid air tubes.

3. The fluid dispensing system of claim 1, wherein an axis of the mount opening intersects an axis of the first tube opening.

4. The fluid dispensing system of claim 3, wherein the axis of the mount opening is orthogonal to the axis of the first tube opening.

5. The fluid dispensing system of claim 1, wherein the dispensing module is mounted to the second side of the manifold.

6. The fluid dispensing system of claim 1, wherein the quick release opening does not intersect the second tube opening.

7. The fluid dispensing system of claim 1, wherein the quick-release mechanism comprises a set screw.

8. The fluid dispensing system of claim 7, wherein the set screw is attached to the manifold within the mount opening with the set screw in each of a secured position, where the set screw is engaged with the first air tube, and an unsecured opposition, where the set screw is disengaged from the first air tube.

9. The fluid dispensing system of claim 8, wherein the dispensing module is mounted to one of the second side of the manifold and a third side of the manifold.

10. The fluid dispensing system of claim 1, further comprising:
    a piston disposed within the dispensing module, the piston configured to be actuated between an open position, where liquid adhesive is dispensed from the dispensing module, and a closed position, where liquid adhesive is prevented from exiting the dispensing module; and
    a spring disposed within the dispensing module, the spring biasing the piston to a closed position, such that the dispensing module is normally closed;
    wherein a first portion of compressed air is directed to the dispensing module by the solenoid assembly through the first air tube and a first flow path in the manifold; and
    wherein the first portion of compressed air is configured to actuate the piston from the closed position to the open position.

11. The fluid dispensing system of claim 10, wherein:
    a second portion of compressed air is directed to the dispensing module though the second air tube and a second flow path in the manifold; and
    the second portion of compressed air is configured to actuate the piston from the open position to the closed position.

12. A liquid adhesive dispensing system comprising:
    a container for storing adhesive pellets;
    a melter capable of heating the adhesive pellets received from the container into a liquid adhesive; and
    a dispensing system configured to receive the liquid adhesive from the melter and to apply the liquid adhesive, the dispensing system comprising:
    a manifold including a fluid outlet, a first tube opening extending into a first side of the manifold, and a second tube opening extending into the first side of the manifold; and a mount opening extending into a second side of the manifold and intersecting with the first tube opening;

a dispensing module fluidly connected to the manifold and configured to receive a liquid adhesive from a fluid outlet of the manifold and to dispense the liquid adhesive;

a solenoid assembly mounted to the manifold by a first air tube and a second air tube, wherein the solenoid assembly is configured to selectively direct air to the dispensing module to actuate the dispensing module between an open position and a closed position;

wherein the first air tube extends into the first tube opening and the second air tube extends into the second tube opening;

wherein a quick release mechanism is mounted in the mount opening, engages the first air tube, and does not engage the second air tube, such that the quick release mechanism is configured to directly secure the first air tube to the manifold and to indirectly secure the solenoid assembly and second air tube to the manifold by the first air tube.

13. The liquid adhesive dispensing system of claim 12, wherein an axis of the mount opening intersects an axis of the first tube opening.

14. The liquid adhesive dispensing system of claim 13, wherein the axis of the mount opening is orthogonal to the axis of the first tube opening.

15. The liquid adhesive dispensing system of claim 12, wherein the dispensing module is mounted to the second side of the manifold.

16. The liquid adhesive dispensing system of claim 12, wherein a power cord extends into the manifold to provide power to heating elements disposed in the manifold.

17. The liquid adhesive dispensing system of claim 16, wherein the quick-release mechanism comprises a set screw.

18. The liquid adhesive dispensing system of claim 17, wherein the set screw is attached to the manifold within the mount opening with the set screw in each of a secured position, where the set screw is engaged with the first air tube, and an unsecured opposition, where the set screw is disengaged from the first air tube.

19. The liquid adhesive dispensing system of claim 18, wherein the dispensing module is mounted to one of the second side of the manifold and a third side of the manifold.

20. A method comprising:
dismounting a solenoid assembly from a manifold of a liquid adhesive dispenser by:
rotating a quick-release mechanism in a first direction within a mount opening extending into the manifold, thereby disengaging the quick-release mechanism from a first air tube of the solenoid assembly; and
pulling the solenoid assembly off of the manifold, thereby removing the first air tube from a first tube opening extending into the manifold, and further removing a second air tube from a second tube opening extending into the manifold;
mounting the solenoid assembly to the manifold by:
positioning the solenoid assembly to align the first air tube with the first air opening and to align the second air tube with the second air opening;
shifting the solenoid assembly to insert the first air tube in the first air opening and insert the second air tube in the second air opening; and
rotating the quick-release mechanism in a second direction within the mount opening, thereby engaging the quick-release mechanism with the first air tube;
directing air through the first air tube and the second air tube to actuate a dispensing module between an open state, where liquid adhesive flows out of the dispensing module, and a closed state, where the liquid adhesive is prevented from flowing out of the dispensing module;
wherein the quick-release mechanism directly secures the first air tube to the manifold and indirectly secures the second air tube and the solenoid assembly to the manifold by the first air tube.

\* \* \* \* \*